United States Patent
Seemann et al.

(10) Patent No.: US 12,318,191 B2
(45) Date of Patent: Jun. 3, 2025

(54) SYSTEMS AND METHODS FOR MONITORING PATIENT MOVEMENT

(71) Applicant: Mazor Robotics Ltd., Caesarea (IL)

(72) Inventors: Ziv Seemann, Beit Ytzhack (IL); Gal Barazani, Haifa (IL); Bat-el Kagan, Natanya (IL); Amir Keret, Atlit (IL); Adi Sandelson, Givatayim (IL)

(73) Assignee: Mazor Robotics Ltd., Caesarea (IL)

( * ) Notice: Subject to any disclaimer, the term of this patent is extended or adjusted under 35 U.S.C. 154(b) by 154 days.

(21) Appl. No.: 17/225,382

(22) Filed: Apr. 8, 2021

(65) Prior Publication Data
US 2022/0322973 A1    Oct. 13, 2022

(51) Int. Cl.
*A61B 5/11* (2006.01)
*A61B 5/00* (2006.01)

(52) U.S. Cl.
CPC .......... *A61B 5/1116* (2013.01); *A61B 5/0017* (2013.01); *A61B 5/0022* (2013.01)

(58) Field of Classification Search
None
See application file for complete search history.

(56) References Cited

U.S. PATENT DOCUMENTS

| 8,401,616 B2 | 3/2013 | Verard et al. |
| 2012/0330154 A1 | 12/2012 | Beasley et al. |
| 2014/0206990 A1* | 7/2014 | Epstein .................. A61B 90/37 600/587 |
| 2019/0046232 A1 | 2/2019 | Tokuda et al. |
| 2019/0090955 A1* | 3/2019 | Singh .................... A61B 17/00 |
| 2019/0321657 A1* | 10/2019 | Hale .................... H04N 13/254 |

FOREIGN PATENT DOCUMENTS

| WO | WO 2019/177711 | 9/2019 |
| WO | WO 2020/072335 | 4/2020 |
| WO | WO 2020/105049 | 5/2020 |

OTHER PUBLICATIONS

International Search Report and Written Opinion for International (PCT) Patent Application No. PCT/IL2022/050360, dated Jul. 27, 2022, 15 pages.

* cited by examiner

*Primary Examiner* — Aurelie H Tu
(74) *Attorney, Agent, or Firm* — Sheridan Ross P.C.

(57) ABSTRACT

Systems and methods for monitoring patient movement are provided. A first dataset containing information about a first tracking device and a second tracking device may be received. A second dataset containing information about the first tracking device and the second tracking device may be received. The first dataset and the second dataset may be compared to determine if a relative pose of the first tracking device and the second tracking device has changed. A notification may be generated when the relative pose of the first tracking device and the second tracking device has changed.

19 Claims, 6 Drawing Sheets

SYSTEMS AND METHODS FOR MONITORING PATIENT MOVEMENT

FIELD

The present technology generally relates to monitoring patient movement during a surgical procedure, and relates more particularly to monitoring relevant movement between a patient and a table on which the patient is positioned.

BACKGROUND

Surgical robots may assist a surgeon or other medical provider in carrying out a surgical procedure, or may complete one or more surgical procedures autonomously. Imaging may be used by a medical provider for diagnostic and/or therapeutic purposes. Patient position may change over the duration of the surgical procedure.

SUMMARY

Example aspects of the present disclosure include:

A method/system for monitoring patient movement according to at least one embodiment of the present disclosure comprises a first tracking device configured to be affixed to a table; a second tracking device configured to be affixed to an anatomical element, the anatomical element having a pose relative to the table; at least one processor; and at least one memory storing instructions for execution by the at least one processor that, when executed, cause the at least one processor to: receive a first dataset, the first dataset containing information about the first tracking device and the second tracking device, receive a second dataset, the second dataset containing information about the first tracking device and the second tracking device, compare the first dataset and the second dataset to determine if a relative pose of the first tracking device and the second tracking device has changed, and generate a notification when the relative pose of the first tracking device and the second tracking device has changed.

Any of the aspects herein, further comprising: a user interface, and wherein the memory stores additional instructions for execution by the at least one processor that, when executed, further cause the at least one processor to: cause the notification to be displayed on the user interface.

Any of the aspects herein, wherein the notification includes instructions for performing one or more verification steps.

Any of the aspects herein, wherein the memory stores additional instructions for execution by the at least one processor that, when executed, further cause the at least one processor to: determine a spatial relationship between a patient and the second tracking device.

Any of the aspects herein, wherein the one or more verification steps includes at least one of verifying a pose of one or more anatomical elements using a probe or redetermining the spatial relationship between the patient and the second tracking device.

Any of the aspects herein, wherein the anatomical element is a vertebra.

Any of the aspects herein, further comprising: a navigation system comprising an optical imaging device, the optical imaging device configured to obtain the first dataset and the second dataset.

Any of the aspects herein, wherein the second tracking device comprises a plurality of tracking devices.

A method/system for monitoring patient movement according to at least one embodiment of the present disclosure comprises a first tracking device configured to be affixed to a table; a second tracking device configured to be affixed to a robot, the robot having a pose relative to the table; at least one processor; and at least one memory storing instructions for execution by the at least one processor that, when executed, cause the at least one processor to: receive a first dataset, the first dataset containing information about the first tracking device and the second tracking device, receive a second dataset, the second dataset containing information about the first tracking device and the second tracking device, compare the first dataset and the second dataset to determine if a relative pose of the first tracking device and the second tracking device has moved, and generate a notification when a relative pose of the first tracking device and the second tracking device has moved.

Any of the aspects herein, wherein the second tracking device is integrated with the robot.

Any of the aspects herein, further comprising: a user interface, and wherein the memory stores additional instructions for execution by the at least one processor that, when executed, further cause the at least one processor to: cause the notification to be displayed on the user interface.

Any of the aspects herein, wherein the notification includes instructions for performing one or more verification steps.

Any of the aspects herein, further comprising: a navigation system comprising an optical imaging device, the optical imaging device configured to obtain the first dataset and the second dataset.

Any of the aspects herein, wherein the robot is affixed to the patient positioned on the table and the memory stores additional instructions for execution by the at least one processor that, when executed, further cause the at least one processor to: register a patient to a preoperative image.

Any of the aspects herein, wherein the one or more verification steps includes at least one of verifying a pose of one or more anatomical elements using a probe or re-registering the patient to the preoperative image.

Any of the aspects herein, wherein the first dataset and the second dataset comprises image data.

Any of the aspects herein, wherein the first dataset and the second dataset comprises sensor data.

A method/system for monitoring patient movement according to at least one embodiment of the present disclosure comprises registering at least one anatomical element to a preoperative image; receiving a first dataset, the first dataset including information about a first tracking device and a second tracking device, the first tracking device affixed to an operating table and the second tracking device affixed to the at least one anatomical element, each of the at least one anatomical element having a pose relative to the table; receiving a second dataset, the second dataset including information about the first tracking device and the second tracking device; comparing the first dataset and the second dataset to determine if a relative pose of the first tracking device and the second tracking device has changed; and generating a notification when the relative pose of the first tracking device and the second tracking device has changed.

Any of the aspects herein, wherein the notification is displayed on a user device, the notification including instructions for performing one or more verification steps.

Any of the aspects herein, wherein the one or more verification steps includes at least one of verifying a pose of one or more anatomical elements using a probe or re-registering the at least one anatomical element to the preoperative image.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10x Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

A registration of a patient to a navigation system or a navigated item (such as, for example, a tracking marker) may occur, for example, prior to a start of a surgical operation. In some embodiments, the registration may include scanning the patient and the navigated item to determine a spatial correlation between the patient and the navigated item. Throughout the operation, it is valuable to know if the registration is valid and whether the patient has moved since the registration. If the patient has moved, then the registration or correlation of the navigated item or navigation system to the patient may no longer be accurate, and an anatomical element (such as, for example, an organ) on which the surgical procedure is to be performed may be in the wrong location. This may result in, for example, performing a surgical procedure in an inaccurate location. For example, if a vertebra has moved during an operation but the registration used to guide a surgical robot is incorrectly believed to still be accurate, then the robot may be commanded to drill into the wrong portion of the vertebra.

In particular, in the spinal region, since the spine has flexibility, a robot mounted at a certain location and having a certain flexibility can induce movement on a clinically relevant location without knowledge to a user such as, for example, a surgeon or medical provider. For example, drilling at a pelvic area where a robot is fixed to a sacrum using a "Schantz pin" may induce movement or shift the spinal region without indication to the user that the shift or movement has occurred. Thus, it is desirable to monitor movement of the patient relative to a table or a bed on which the patient is positioned to verify that the registration is still accurate during the operation.

In at least one embodiment of the present disclosure, a tracking marker may be attached to a patient (whether directly on an anatomical element of the patient or on a robot that is fixedly connected to the patient (such as, for example, via an anatomical element)). A tracking marker may also be attached to an operating table or bed on which the patient is positioned. During a surgical procedure, it is assumed that the table and the patient (e.g., the tracking marker attached to the patient) are not intentionally moved relative to each other or if they are moved intentionally by, for example, a surgical team, then the movement is known to the surgical team. If unintentional movement is detected between the patient and the bed, there is a chance that the patient anatomy has moved. When such unintentional movement is detected, a user such as, for example, a surgeon or other medical provider may be alerted and prompted to troubleshoot the registration. Troubleshooting the registration may include, for example, using a probe to test whether one or more anatomical elements, or any component of a robot, is/are in a correct position vis-à-vis the registration. If so, then the registration remains accurate; if not, then the registration is inaccurate and must be updated.

Embodiments of the present disclosure provide technical solutions to one or more of the problems of (1) detecting movement of a patient during a surgical procedure, (2) detecting relative movement of a patient and an operating table on which the patient is positioned, (3) detecting relative movement of a robot and a patient to which the robot is fixed, (4) detecting relative movement of a robot and an operating table, (5) validating a registration between a patient and a navigation system and/or a navigated item, and/or (6) increasing patient safety.

Figure 1:
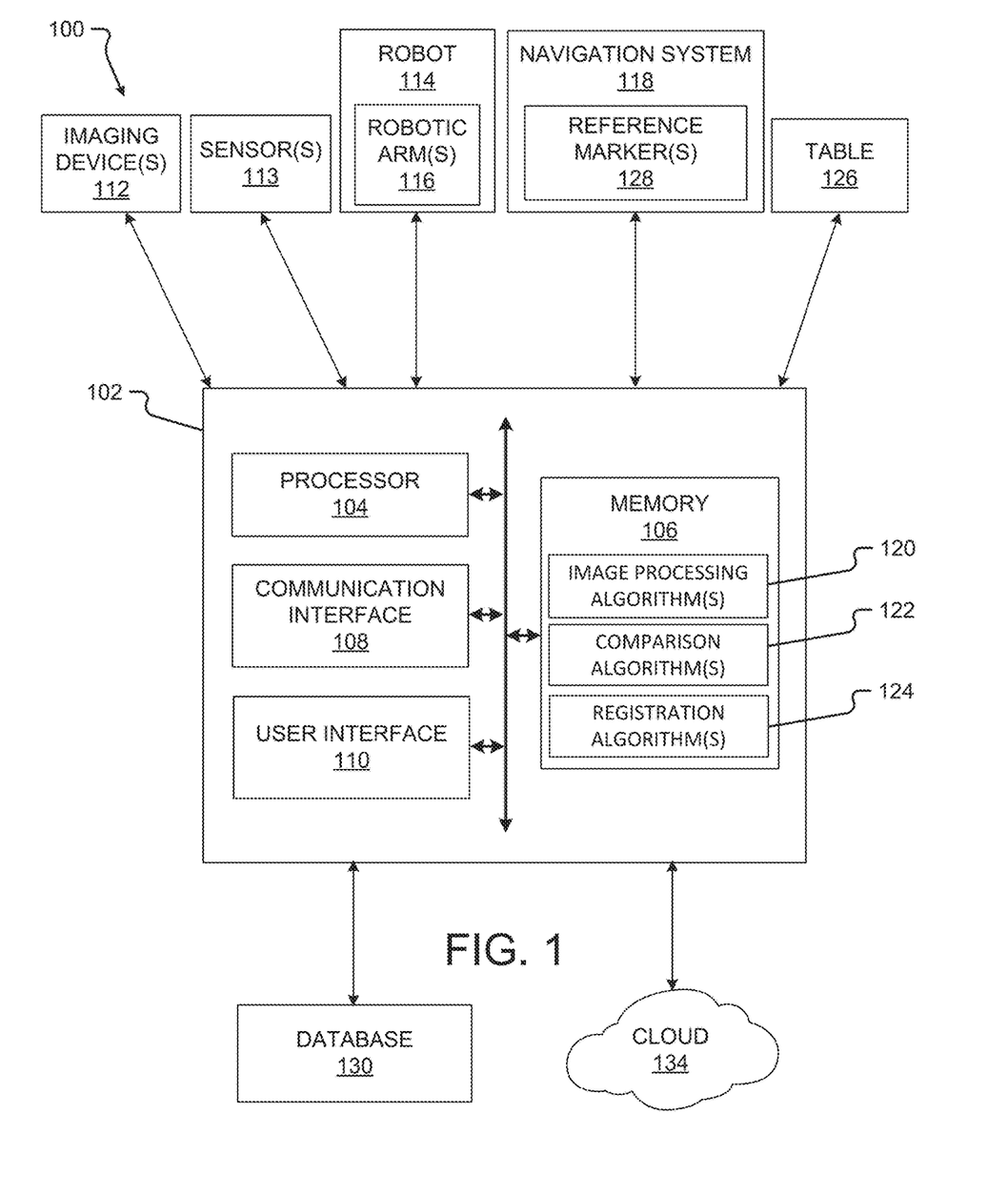
FIG. 1 is a block diagram of a system according to at least one embodiment of the present disclosure.

Turning first to FIG. 1, a block diagram of a system 100 according to at least one embodiment of the present disclosure is shown. The system 100 may be used to monitor patient movement and/or carry out one or more other aspects of one or more of the methods disclosed herein. The system 100 comprises a computing device 102, one or more imaging devices 112, one or more sensors 113, a robot 114, a navigation system 118, a table 126, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the sensors 113, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 400 and/or 600 described herein, or of any other methods. The memory 106 may store, for example, one or more image processing algorithms 120, one or more comparison algorithms 122, and/or one or more registration algorithms 124. Such instructions or algorithms may, in some embodiments, be organized into one or more applications, modules, packages, layers, or engines. The algorithms and/or instructions may cause the processor 104 to manipulate data stored in the memory 106 and/or received from or via the imaging device 112, the sensors 113, the robot 114, the database 130, and/or the cloud 134.

The computing device 102 may also comprise a communication interface 108. The communication interface 108 may be used for receiving image data, dataset(s), or other information from an external source (such as the imaging device 112, the sensors 113, the robot 114, the navigation system 118, the database 130, the cloud 134, and/or any other system or component not part of the system 100), and/or for transmitting instructions, images, or other information to an external system or device (e.g., another computing device 102, the imaging device 112, the sensors 113, the robot 114, the navigation system 118, the database 130, the cloud 134, and/or any other system or component not part of the system 100). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computing device 102.

The imaging device 112 may be operable to image anatomical feature(s) (e.g., a bone, veins, tissue, etc.), objects in an operating room (e.g., one or more reference markers or tracking devices, etc.), and/or other surgically relevant objects to yield image data (e.g., image data depicting or corresponding to a bone, veins, tissue, reference markers, tracking devices, etc.). "Image data" as used herein refers to the data generated or captured by an imaging device 112, including in a machine-readable form, a graphical/visual form, and in any other form. In various examples, the image data may comprise data corresponding to an object and/or an anatomical feature of a patient, or to a portion thereof. The image data may be or comprise a preoperative image, an intraoperative image, a postoperative image, or an image taken independently of any surgical procedure. The imaging device 112 may be capable of taking a 2D image or a 3D image to yield the image data.

The imaging device 112 may be or comprise, for example, an optical camera, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MM) scanner, an optical coherence tomography (OCT) scanner, an endoscope, a microscope, a thermographic camera (e.g., an infrared camera), a radar system (which may comprise, for example, a transmitter, a receiver, a processor, and one or more antennae), or any other imaging device 112 suitable for obtaining images of an anatomical feature of a patient or any object or component. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The system 100 includes the one or more sensor(s) 113. The sensor 113 is operable to detect reference markers or tracking devices 128 disposed on, for example, the table 126, the robot 114, a patient, or any other component of the system 100. The sensor 113 is operable to yield one or more datasets such as, for example, a first dataset and/or a second dataset. Each dataset may include information about detected reference markers or tracking devices 128. In embodiments where the sensor 113 is the imaging device 112, the dataset(s) may comprise image data. In other embodiments, the dataset(s) may comprise any type of data including, for example, sensor data. In some embodiments, the same sensor 113 may be used to obtain a first dataset and a second dataset or any number of datasets. In other embodiments, a first sensor 113 may be used to obtain the first dataset and a second sensor 113 may be used to obtain the second dataset. It will also be appreciated that any number of sensors may be used to obtain any number of datasets.

The sensor 113 may be, for example, an imaging device such as the imaging device 112 described above, an optical camera, an infrared camera, a 3D camera system, a stereoscopic vision system, or any other sensor that can detect the reference markers or tracking devices 128. In some examples, the reference markers or tracking devices 128 may be active markers and the sensor 113 may be configured to sense the reference markers or tracking devices 128 when the reference markers or tracking devices 128 are activated (by the processor 104, for example). In such examples, the reference markers or tracking devices 128 may be infrared light emitting diodes and the sensor 113 may be an infrared camera configured to sense when the reference markers or tracking devices 128 emit infrared light. In other examples, the reference markers or tracking devices 128 may be passive markers. For example, the reference markers or tracking devices 128 may be reflective markers and the sensor 113 may be an optical camera.

The sensor 113 may comprise a dedicated processor for executing instructions stored in a dedicated memory of the sensor 113, or the sensor 113 may simply be configured to transmit data collected therewith to the computing device 102 or to another component of the system 100. Although shown in FIG. 1 as being in communication only with the computing device 102, in some embodiments, the sensor 113 may be in communication with any one or more of the computing device 102, the robot 114, the navigation system 118, the database 130, and/or the cloud 134. Also, in some embodiments, the computing device 102 may comprise the sensor 113, while in other embodiments, the navigation system 118 may comprise the sensor 113. In still other embodiments, the robot 114 may comprise the sensor 113.

The sensor 113 may be positioned directly above an operating table or portion thereof, or above and to one side of an operating table or portion thereof, or in another convenient position within an operating room or other room. The sensor 113 may be positioned at a location selected to provide the sensor 113 with a clear and/or unobstructed view of the reference markers or tracking devices 128 during operation thereof. In some embodiments, the sensor 113 is fixed, while in other embodiments, the sensor 113 may be precisely movable (whether manually or automatically) in one or more directions.

The sensor 113 may be configured to capture data regarding sensed reference markers or tracking devices 128 only at a given moment in time. For example, where the sensor 113 is a camera, the sensor 113 may be configured to capture still images comprising one or more reference markers or tracking devices 128. The sensor 113 may be configured to capture such data at periodic intervals, or when commanded by a user (e.g., via a user interface 110), or upon a signal (generated either autonomously or in response to user input) from the computing device 102, the robot 114, and/or the navigation system 118.

The sensor 113 may additionally or alternatively be operable to capture data corresponding to the reference markers or tracking devices 128 continuously, in real-time. In such embodiments, the sensor 113 may provide a stream of real-time sensor data to the computing device 102, which may continuously process the sensor data to detect the reference markers or tracking devices 128 therein. In some embodiments, the sensor 113 may comprise more than one sensor 113.

The robot 114 may be any surgical robot or surgical robotic system. The robot 114 may be or comprise, for example, the Mazor X™ Stealth Edition robotic guidance system. In some embodiments, the robot 114 may be used with a biopsy device. The robot 114 may include the imaging device 112 (which may be, for example, an optical camera, an ultrasound scanner, a microscope, an O-arm, a C-arm, a G-arm, or any other device utilizing X-ray-based imaging, an MRI scanner, an OCT scanner, an endoscope, a microscope, a thermographic camera, or a radar system). The robot 114 may be configured to position the imaging device 112 at one or more precise position(s) and orientation(s), and/or to return the imaging device 112 to the same position (s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. In some embodiments, the robot 114 may be fixedly connected to a patient. For example, a pin or screw may be supported by the robot 114 and fixed to an anatomical element of a patient, thereby fixedly connecting the robot 114 to the patient. As will be described in more detail below, by fixedly connecting the robot 114 to a patient, patient movement may be monitored by a reference marker or tracking devices 128 disposed on the robot 114 as movement by the patient will be transferred to the robot 114 via the fixed connection.

The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

The table 126 may be any operating table 126 configured to support a patient during a surgical procedure. The table 126 may include any accessories mounted to or otherwise coupled to the table 126 such as, for example, a bed rail, a bed rail adaptor, an arm rest, an extender, or the like. The operating table 126 may be stationary or may be operable to maneuver a patient (e.g., the operating table 126 may be able to move). In some embodiments, the table 126 has two positioning degrees of freedom and one rotational degree of freedom, which allows positioning of the specific anatomy of the patient anywhere in space (within a volume defined by the limits of movement of the table 126). For example, the table 126 can slide forward and backward and from side to side, and can tilt (e.g., around an axis positioned between the head and foot of the table 126, and extending from one side of the table 126 to the other) and/or roll (e.g., around an axis positioned between the two sides of the table 126, and extending from the head of the table 126 to the foot thereof). In other embodiments, the table 126 can bend at one or more areas (which bending may be possible due to, for example, the use of a flexible surface for the table 126, or by physically separating one portion of the table 126 from another portion of the table 126 and moving the two portions independently). In at least some embodiments, the table 126 may be manually moved or manipulated by, for example, a surgeon or other user, or the table 126 may comprise one or more motors, actuators, and/or other mechanisms configured to enable movement and/or manipulation of the table 126 by the processor 104. The robot 114 may be independent of and unattached to the table 126 in some embodiments. In other words, the robot 114 may be manipulated and moved separately from the table 126. In such embodiments, the robot 114 may be secured to one or more of a floor, wall, and/or ceiling of an operating room, or to any structure affixed to any of the foregoing. In other embodiments, the robot 114 may be attached to the table 126.

In some embodiments, reference markers or tracking devices 128 (i.e., navigation markers) may be placed on the robot 114 (including, e.g., on the robotic arm 116), the imaging device 112, the table 126 (or any accessory mounted or otherwise coupled to the table 126), an anatomical element, or any other object in the surgical space. In some embodiments, the reference markers or tracking devices 128 are passive markers. In other embodiments, the reference markers or tracking devices 128 are active markers. In still other embodiments, the reference markers or tracking devices 128 may be active wireless markers. In further embodiments, the reference markers or tracking devices 128 may include a combination of passive and active markers.

The reference markers or tracking devices 128 may be tracked by the navigation system 118 using, for example, the sensor 113, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The reference markers or tracking devices 128 may comprise one or more arms extending in one or more directions. One or more tracking elements (e.g., reflective spheres, light-emitting diodes (LEDs), infrared-emitting devices (IREDs), optical patterns, shapes, etc.) may be provided on any given reference marker or tracking device 128. The elements may be arranged in two dimensions or three dimensions such that analysis of a perceived distance (e.g., as reflected in image data) between or among various tracking elements on a given reference marker or tracking device 128 may yield a precise determination of a three-dimensional pose of the reference marker tracking device 128.

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system may comprise one or more electromagnetic sensors. In various embodiments, the navigation system 118 may be used to track a position and orientation (i.e., pose) of the imaging device 112, the robot 114 and/or robotic arm 116, one or more reference markers or tracking devices 128, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The system 100 or similar systems may be used, for example, to carry out one or more aspects of any of the methods 400 and/or 600 described herein. The system 100 or similar systems may also be used for other purposes.

Below, the description of FIGS. 2-4 relates to embodiments in which relative movement of a patient and a table is tracked by tracking the table and the patient directly or tracking a rigid portion of a robot fixedly connected to the patient. Further below, the description of FIGS. 5-6 relates to embodiments in which movement of a robot is tracked relative to a table to detect undesired movement of the robot, whether caused by the robot or movement of the patient or table.

Figure 2:
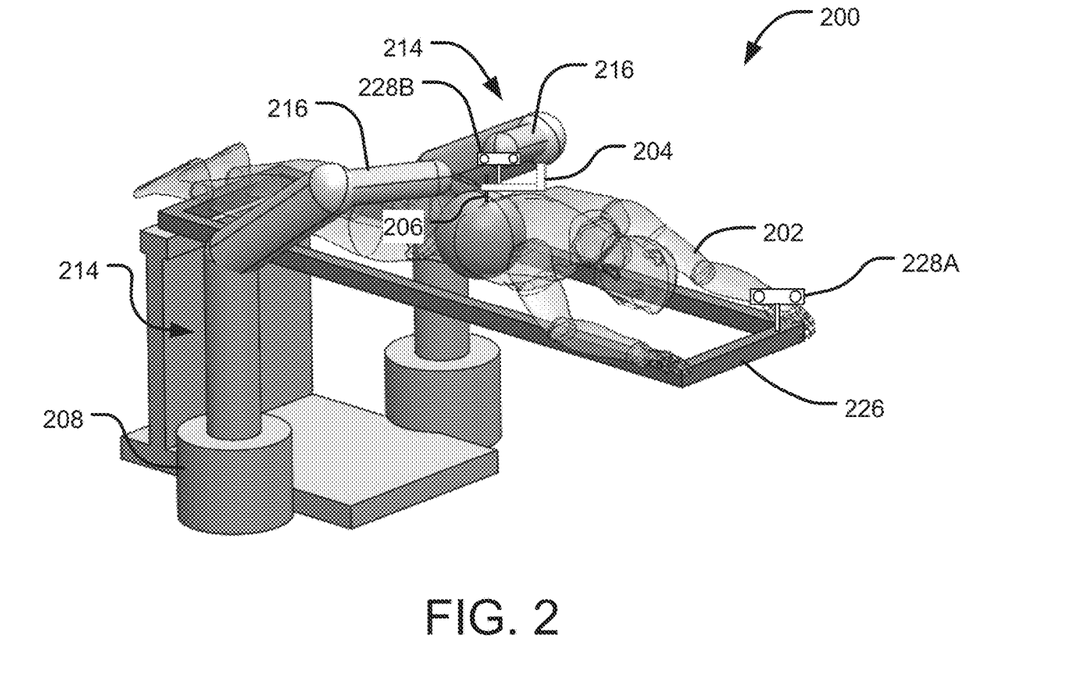
FIG. 2 is an image of an operating table, a patient, and a robot according to at least one embodiment of the present disclosure.

Turning to FIG. 2, at least a portion of a surgical room 200 is illustrated including two robots 214 (each of which may be the same as or similar to the robot 114 described above) each having a robotic arm 216 (which may be the same as or similar to the robotic arm 116), an operating table 226 (which may be the same as or similar to the table 126 described above), and a patient 202 laying prone on the table 226. It will be appreciated that in other instance, the patient 202 may be laying in any position such as, for example, supine, lateral, or lateral decubitus. In some embodiments the patient 202 may remain in the same position for a duration of a surgical procedure. In other embodiments, the patient 202 may change positions during the surgical procedure. Though two robots 214 and two robotic arms 216 are shown, it will be appreciated that only one robot 214 and/or one robotic arm 216 may be used during a surgical procedure. It will also be appreciated that more than one robot 214, more than one robotic arm 216, or a robot 214 with more than one robotic arm 216 may be used during a surgical procedure.

In the illustrated embodiment, a first tracking device 228A is attached to the table 226 and a second tracking device 228B is attached to a rigid connector 204 of one of the robotic arms 216. Each of the first tracking device 228A and the second tracking device 228B may be the same as or similar to the reference marker or tracking device 128, described above. It will be appreciated that each of the first tracking device 228A and/or the second tracking device 228B may include one or more tracking devices.

The second tracking device 228B is attached to a portion of the robot 214 that is fixedly connected to the patient 202. In some embodiments the second tracking device 228B may be integrated with the robot 214. In the illustrated embodiment, the robot 214 includes the rigid connector 204 connecting the robot 214 to the patient 202 via a pin or a screw 206. In some embodiments, the pin or screw 206 may be fixed to a spinal region (such as, for example, a vertebra), thereby fixedly connecting the robot 214 to the patient 202. In other embodiments, the pin 206 may be a "Schantz" pin and fixed to a pelvic bone. In other embodiments, the robot 214 may be fixedly connected to the patient 202 using any type of connector. For example, the robot 214 may be fixedly connected to the patient 202 via a screw. In the illustrated embodiment, the second tracking device 228B is attached to the rigid connector 204. In other embodiments, the second tracking device 228B may be attached to any portion of the robot 214 that is fixed (e.g., may not experience any intentional movement) to the patient. For example, while the robot 214 is floor-mounted via a base 208, in embodiments where a robot is mounted to a patient (e.g., such that the patient's body supports the weight of the robot), the second tracking device 228B may be mounted to a base or other non-moving portion of the robot. By attaching the second tracking device 228B to the robot 214, movement of the patient 202 can be monitored. For example, if the patient 202 experiences movement relative to the table 226, the movement will be transferred to the robot 214 (whether via the rigid connector 204 or otherwise), which in turn will cause the robot 214 to move, and thus, the second tracking device 228B will also move (relative to the first tracking device 228A).

Figure 3:
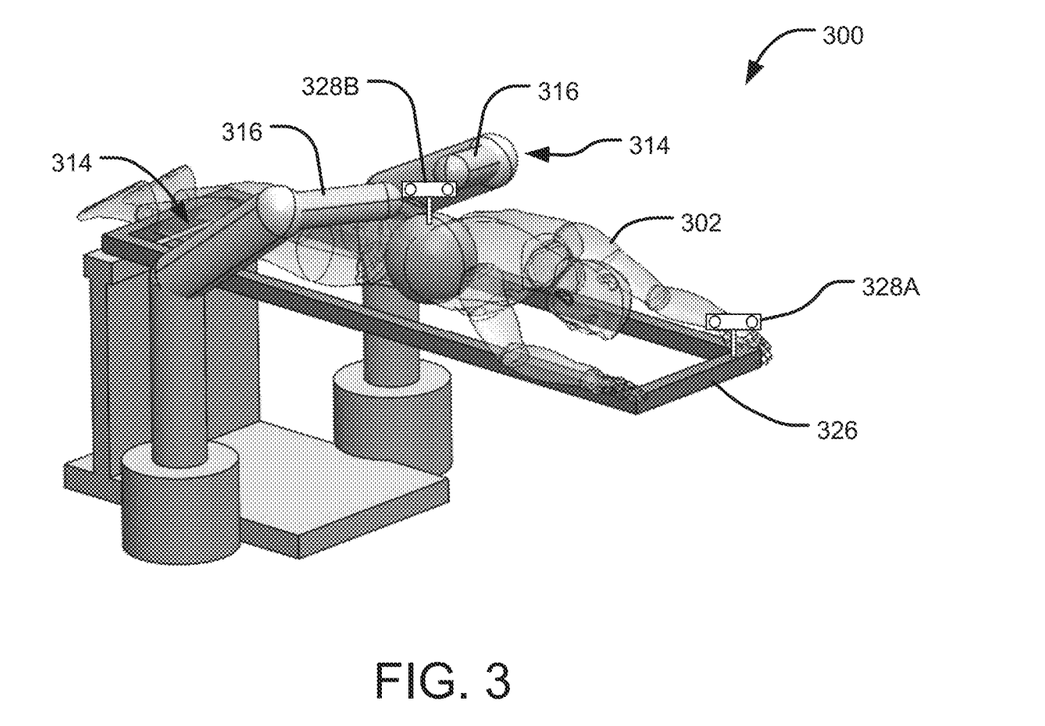
FIG. 3 is an image of an operating table, a patient, and a robot according to at least one embodiment of the present disclosure.

Turning to FIG. 3, similar to FIG. 2 above, at least a portion of a surgical room 300 is illustrated including two robots 314 (each of which may be the same as or similar to the robot 114 and/or 214 described above) each having a robotic arm 316 (which may be the same as or similar to the robotic arm 116 and/or 216), an operating table 326 (which may be the same as or similar to the tables 126 and/or 226 described above), and a patient 302 laying prone on the table 326. Though two robots 314 and two robotic arms 316 are shown, it will be appreciated that only one robot 314 and/or one robotic arm 316 may be used during a surgical procedure. It will also be appreciated that more than one robot 314, more than one robotic arm 316, or a robot 314 with more than one robotic arm 316 may be used during a surgical procedure in the surgical room 300.

In the illustrated embodiment, a first tracking device 328A is attached to the table 326 and a second tracking device 328B is attached to an anatomical element of the patient 302. The anatomical element may be, for example, a vertebra or a sacrum. Each of the first tracking device 328A and the second tracking device 328B may be the same as or similar to the reference marker or tracking device 128 and/or 228, described above. It will be appreciated that each of the first tracking device 328A and/or the second tracking device 328B may include one or more tracking devices. While the second tracking device 228B of FIG. 2 is connected to the robot 214 (or a rigid connector 204 extending from the robot 214 to the patient 202), the second tracking device 328B of FIG. 3 is connected directly to the patient. As a result, movement of the patient 302 relative to the table 326 will cause movement of the second tracking device 328B relative to the first tracking device 328A.

As will be described in detail below, the first tracking device 228A, 328A and the second tracking device 228B, 328B may be used to determine and/or monitor movement of the patient 202, 302 relative to the table 226, 326. During a procedure, a relative pose between the first tracking device 228A, 328A and the second tracking device 228B, 328B may be monitored (by, for example, a navigation system such as the navigation system 118) for changes. Changes in the relative pose may indicate that the patient 202, 302 (or the table 226, 326 or the robot 214, 314) has moved, and thus, an initial registration of the patient 202, 302 may no longer be accurate. A notification may be generated and communicated to a user such as a surgeon or other medical provider to alert the user of the detected movement (and, as a result of the detected movement, the possible need to update an existing registration or complete a new registration).

Figure 4:
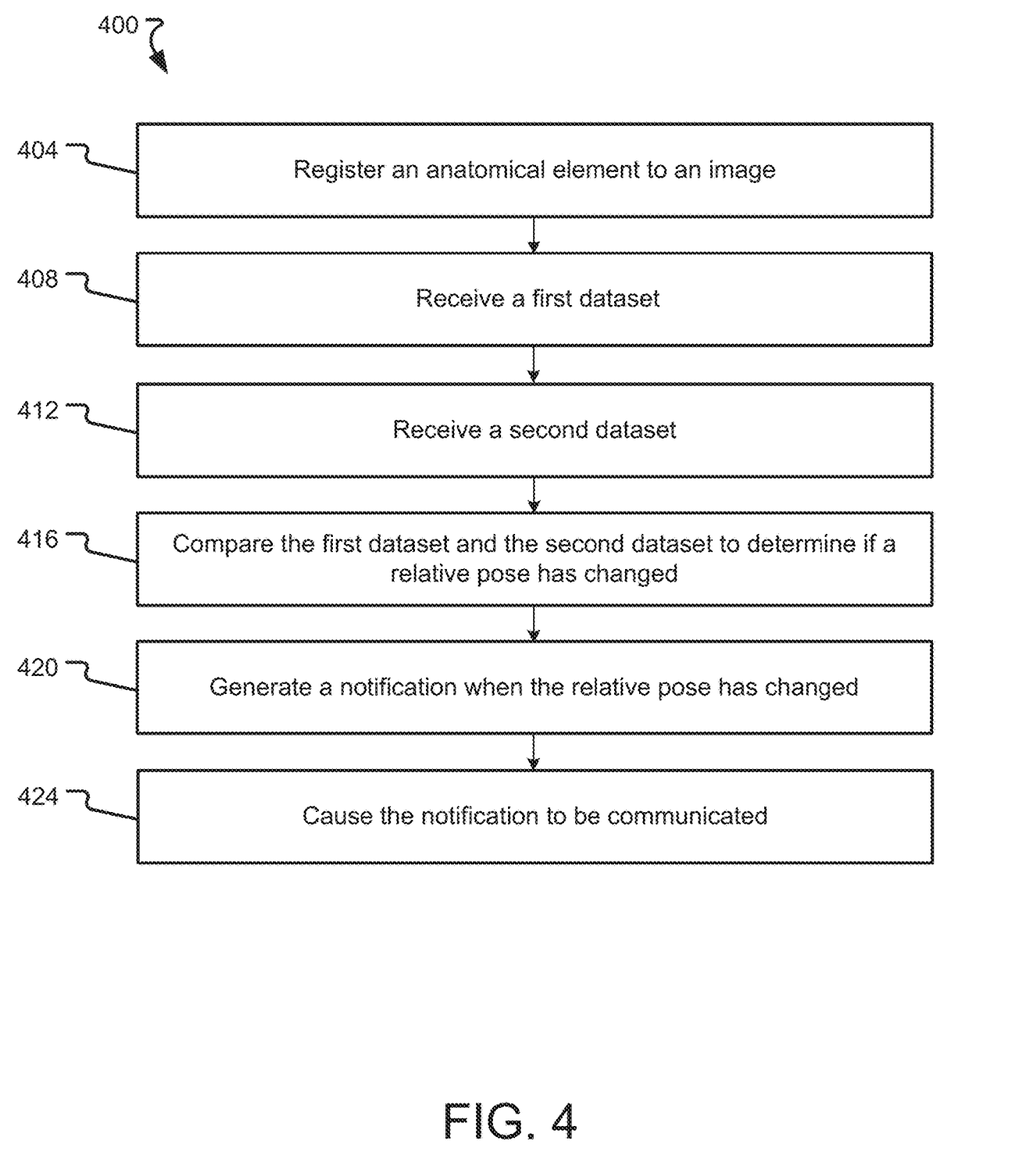
FIG. 4 is a flowchart according to at least one embodiment of the present disclosure.

FIG. 4 depicts a method 400 that may be used, for example, for monitoring patient movement. The method 400 may be used during any surgical procedure(s).

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114, 214, 314) or part of a navigation system (such as a navigation system 118). A processor other than any processor described herein may also be used to execute the method 400. The at least one processor may perform the method 400 by executing instructions stored in a memory such as the memory 106. The instructions may correspond to one or more steps of the method 400 described below. The instructions may cause the processor to execute one or more algorithms, such as an image processing algorithm 120, a comparison algorithm 122, and/or a registration algorithm 124.

The method 400 comprises registering an anatomical element to a preoperative image (step 404). The anatomical element may be, for example, a vertebra. The preoperative image may be obtained from an imaging device such as the imaging device 112. In other instances, the preoperative image may be received from a user interface such as the user interface 110 and/or a communication interface such as the communication interface 108 of a computing device such as the computing device 102, and may be stored in a memory such as the memory 106 of the computing device. Registering the anatomical element may include registering the patient, or a broader portion thereof than just the anatomical element, to the preoperative image. Prior to performing a surgical procedure (whether this occurs, for example, at the beginning of an operation or prior to a specific surgical step), a navigation system such as the navigation system 118 may be used to register a preoperative image of the patient (or a portion thereof) to the patient, so that the preoperative image is aligned with the patient's position on the operating table and any given location in the preoperative image can be correlated to the precise corresponding location on the patient. The registration may be completed using a registration algorithm such as the registration algorithm 124. Registering the anatomical element and/or the patient to the preoperative image may yield a correlation between a patient-based coordinate system and a coordinate system of the navigation system.

In some embodiments, the step 404 may include determining a spatial relationship between an anatomical element or the patient and a navigated item. The navigated item may be, for example, a second tracking device such as the second tracking device 228B, 328B (whether it is affixed to the patient or the robot). Determining the spatial relationship between the anatomical element or the patient and the navigated item may be completed using the registration algorithm.

The method 400 also comprises receiving a first dataset (step 408). The first dataset may be received via a user interface such as the user interface 110 and/or a communication interface such as the communication interface 108 of a computing device such as the computing device 102, and may be stored in a memory such as the memory 106 of the computing device. In some embodiments, the first dataset may be received or obtained from a sensor such as the sensor 113, which may be, for example, an optical camera (which may or may not be part of the navigation system), an infrared camera, a 3D camera system, a stereoscopic vision system, an MRI scanner, a CT scanner, any other X-ray based imaging device, or an ultrasound imaging device. The first dataset may also be generated by and/or received from any other component of a system such as the system 100. In some embodiments, the first dataset may be indirectly received via any other component of the system or a node of a network to which the system is connected. In some embodiments, the first dataset is a first image.

The first dataset may comprise one or more 2D images, one or more 3D images, a 3D model, a combination of one or more 2D images and one or more 3D images, or sensor data from the sensor. In some embodiments, one sensor may be used to obtain the first dataset. In other embodiments, multiple sensors may be used to obtain the first dataset. In examples wherein the first dataset is a first image and more than one image is received or multiple images are used to construct a 3D image, a first imaging device may obtain a first one of the images independently of a second imaging device obtaining a second one of the images. In another example, where the first dataset is a first image, at least a first one of the images may be obtained with a first imaging device and at least a second one of the images may be obtained with a second imaging device.

The first dataset may be processed using a processor such as the processor 104 to identify one or more features in the first image. In embodiments where the first dataset is a first image, the first image may be processed using an imaging processing algorithm such as the image processing algorithm 120. In some embodiments, feature recognition (using, e.g., an edge detection or other feature recognition algorithm) may be used to identify one or more features of, for example, a tracking device or a reference marker. In some embodiments, one or more other objects, such as an anatomical element, a tool, and/or an instrument may additionally or alternatively be identified in the first image. For example, a contour of a vertebra, femur, or other bone may be identified in the image. In other embodiments, segmentation may be used to identify an anatomical element in the image.

The first dataset includes information about at least a portion of the operating room including a first tracking device such as the first tracking device 228A, 328A and a second tracking device such as the second tracking device 228B, 328B. The first tracking device may be attached to a table such as the table 126, 226, 326. In some embodiments, the second tracking device may be attached to a robot such as the robot 114, 214, 314. In such embodiments, the robot may be fixedly connected to a patient positioned on the table. In other embodiments, the second tracking device may be attached to an anatomical element of the patient. In all embodiments, the second tracking device may be used to track movement of the patient relative to the first tracking device.

The method 400 also comprises receiving a second dataset (step 412). The step 412 is the same as or similar to the step 408 with respect to receiving a dataset. The second dataset also includes information about the first tracking device and the second tracking device.

The method 400 also comprises comparing the first dataset and the second dataset to determine if a relative pose has changed (step 416). The relative pose is between the first tracking device and the second tracking device. In some embodiments, a comparison algorithm such as the comparison algorithm 122 may be used to determine if the relative pose has changed.

The comparing may include determining a pose of the first tracking device relative to the second tracking device in the first dataset—using, for example, a processor such as the processor 104—and a pose of the first tracking device relative to the second tracking device in the second dataset. The relative poses of the first tracking device and the second tracking device in the first dataset and the second dataset may be compared by the processor to determine if the relative pose has changed. In other embodiments where the first dataset is a first image and the second dataset is a second image, the comparing may simply include overlaying, by the processor, one of the first image or the second image over the other and aligning one of the first tracking device and the second tracking device in each image. If the other of the first tracking device and the second tracking device does not line up (or, in other words, if both the first and second tracking devices in the first image do not line up with both the first and second tracking devices in the second image), then a determination is made that the relative pose has changed.

The comparing may include comparing a difference in the relative pose between the first dataset and the second dataset to a threshold. For example, in some embodiments where the robot is fixedly connected to the patient, though the connection is assumed to have no relative movement between the robot and the patient, the connection (or pin, or other portion of the fixed connection) may have some flexibility. The threshold may be based on a flexibility of a fixed connection. In other embodiments, whether due to resolution or quality of the first and second datasets, a required level of accuracy and/or precision for the surgical procedure being undertaken, or otherwise, a threshold may be used to prevent a determination of a change in relative pose when the change is insignificant (e.g., clinically irrelevant).

If a change in the relative pose between the table and the patient has occurred, then the patient is assumed to have moved (relative to the table) since the beginning of a surgical procedure (or since the registration completed as described in step 404). The patient's movement may be due to, for example, movement of the table (such as, for example, a change in the angle or tilt of the table, resulting in the patient sliding, rolling, or otherwise moving), movement of the patient independent of any table movement (due to, for example, forces exerted on the patient from a surgeon or other medical provider, or the robot), or movement of the robot. If no change has occurred, then no determination that the relative pose has changed is made, and the registration is assumed to still be accurate.

It will be appreciated that the steps 404-416 may be repeated throughout a surgical procedure to verify that the navigation system is accurate. In some embodiments the steps 404-416 may be repeated prior to a surgical step. In other embodiments the steps 404-416 may be continuously repeated throughout a duration of the surgical procedure to continuously monitor the patient and the table for relative movement. In still, other embodiments, the steps 404-416 may be performed upon input from, for example, a medical provider such as a surgeon.

The method 400 also comprises generating a notification when the relative pose has changed (step 420). The notification may be automatically generated by, for example, a processor such as the processor 104.

The notification may be or comprise an audible notification, a visual notification, a tactile notification, or any other type of notification. The notification may include instructions for performing one or more verification steps. The one or more verification steps may include one or more of verifying a pose of one or more anatomical elements and/or any component on the robot using, for example, a probe such as a navigation probe; confirming that the second tracking device still has the same spatial relationship to the patient (e.g., that the second tracking device has not come loose or otherwise moved relative to the patient); or re-registering the patient to the preoperative image. The notification may also prompt a user to, for example, confirm that the one or more verification steps have been performed and/or to acknowledge the detected change in the relative pose.

The method 400 also comprises causing the notification to be communicated (step 424). In some embodiments, a processor such as the processor 104 may cause the notification to be displayed on a user interface such as the user interface 110. In other embodiments where the notification includes instructions for performing one or more verification steps, the instructions may be displayed on the user interface. In other embodiments, the processor may cause the notification to emit a visual or audible signal such as a beep, color coded light, a flashing light, or the like. Causing the notification to be communicated may also include preventing movement of a robot or causing a robot to cease movement, by, for example, the processor, when a change in the relative pose has changed.

The present disclosure encompasses embodiments of the method 400 that comprise more or fewer steps than those described above, and/or one or more steps that are different than the steps described above.

Figure 5:
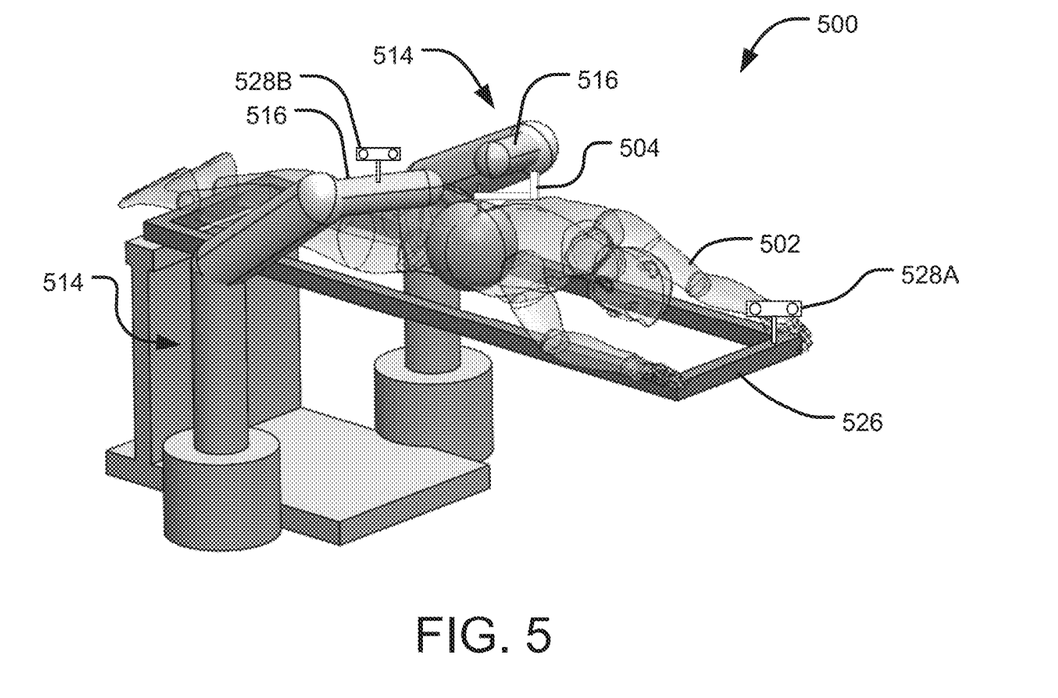
FIG. 5 is an image of an operating table, a patient, and a robot according to at least one embodiment of the present disclosure.

Turning to FIG. 5, at least a portion of a surgical room 500 is illustrated including two robots 514 (each of which may be the same as or similar to the robot 114 or any other robot described herein) each having a robotic arm 516 (which may be the same as or similar to the robotic arm 116 or any other robotic arm described herein), an operating table 526 (which may be the same as or similar to the table 126 or any other table described herein), and a patient 502 laying prone on the table 526. Though two robots 514 and two robotic arms 516 are shown, it will be appreciated that only one robot 514 and/or one robotic arm 516 may be used during a surgical procedure. It will also be appreciated that more than one robot 514, more than one robotic arm 516, or a robot 514 with more than one robotic arm 516 may be used during a surgical procedure.

As shown in the illustrated embodiment, a first tracking device 528A is attached to the table 526 and a second tracking device 528B is attached to one of the robotic arms 516. Each of the first tracking device 528A and the second tracking device 528B may be the same as or similar to the reference marker or tracking device 128 or any other reference marker or tracking device described herein. It will be appreciated that the first tracking device 528A and/or the second tracking device 528B may include one or more tracking devices.

In the illustrated embodiment, the second tracking device 528B is attached to a moving portion of the robot 514 such as, for example, one of the robotic arms 516. In other embodiments, the second tracking device 528B may be attached to any moving portion of the robot 514. In some embodiments the second tracking device 528B may be integrated with the robot 514. By tracking a moving portion of the robot 514, undesired movement of the robotic arm 516 (whether resulting from play in the robotic arm 516, inaccurate or imprecise control of the robotic arm 516, or, in embodiments where the robot 514 is mounted to the patient 502, movement of the patient 502 transferred to the robotic arm 516) may be detected. The embodiment of FIG. 5 may be particularly useful in instances where a line of sight to a tracking device attached to a rigid connector 504, or where a line of sight to a fixed portion of a robot that is mounted to a patient, may be obstructed. The embodiment of FIG. 5 may also be useful where attaching a tracking device to a fixed portion of the robot may be difficult. In any event, the second tracking device 528B may be fixed to a moving portion of the robot, at the cost of less certainty about the cause of any detected change in relative pose of the first and second tracking devices 528A, 528B. Undesired movement of the robotic arm 516 may be determined by comparing an expected pose of the robotic arm 516 (e.g., as reflected in a surgical plan, using instructions that were provided to the robotic arm 516 to cause the robotic arm 516 to assume the pose in question, or based on data obtained from sensors in the robotic arm 516) and an actual pose of the robotic arm 516 (e.g., as reflected in data captured by the navigation system 118 or a sensor such as the sensor 113) after an expected or planned movement of the robotic arm 516 has occurred, as will be described in detail with respect to method 600 in FIG. 6 below.

Figure 6:
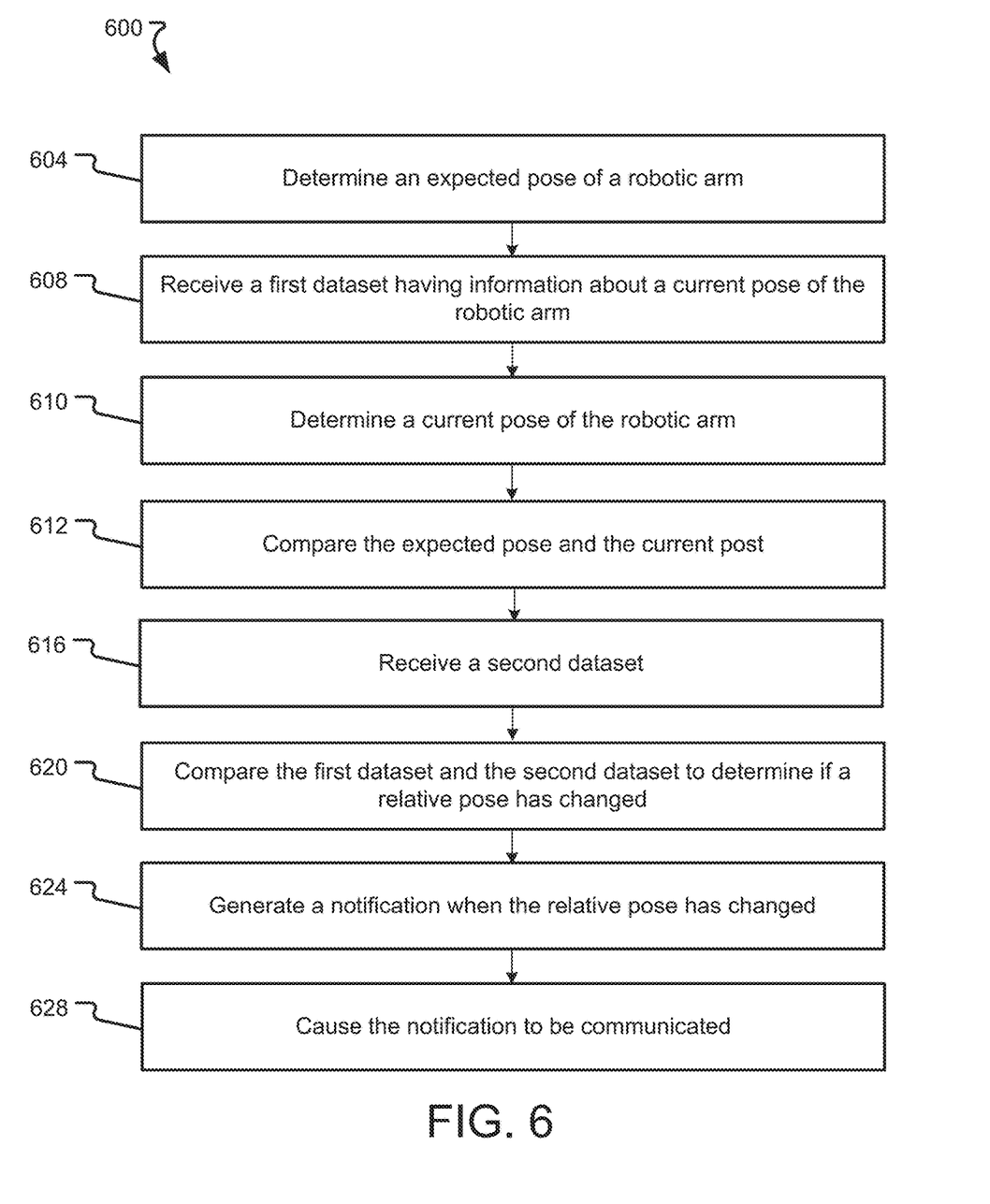
FIG. 6 is a flowchart according to at least one embodiment of the present disclosure.

FIG. 6 depicts a method 600 that may be used, for example, for monitoring patient movement. The method 600 may be used during any surgical procedure(s).

The method 600 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114, 214, 314, 514) or part of a navigation system (such as a navigation system 118). A processor other than any processor described herein may also be used to execute the method 600. The at least one processor may perform the method 600 by executing instructions stored in a memory such as the memory 106. The instructions may correspond to one or more steps of the method 600 described below. The instructions may cause the processor to execute one or more algorithms, such as an image processing algorithm 120, a comparison algorithm 122, and/or a registration algorithm 124.

The method 600 comprises determining an expected pose of a robotic arm (step 604). The robotic arm may be the same as or similar to the robotic arm 116, 216, 316, 516. In some embodiments where, for example, the robotic arm is an accurate robotic arm, an expected pose may be determined by a processor such as the processor 104 using sensor data from the robotic arm. In other embodiments where, for example, the robotic arm is not accurate and a pose cannot be determined directly from the robot, the expected pose may be obtained, for example, from a surgical plan received by a processor such as the processor 104.

The method 600 also comprises receiving a first dataset having information about a current pose of the robotic arm (step 608). The step 608 is the same as or similar to the step 408 described above with respect to receiving a dataset. The first dataset depicts a first tracking device such as the first tracking device 228A, 328A, 528A affixed to a table such as the table 126, 226, 326, 526, and a second tracking device such as the second tracking device 228B, 328B 528B affixed to a moving portion of a robot such as the robot 114, 214, 314, 514 (which robot is either mounted on the patient or secured to the patient using a Schantz pin or otherwise). The moving portion of the robot may be, for example, the robotic arm.

The method 600 also comprises determining a current pose of the robotic arm (step 610). Determining—using, for example, a processor such as the processor 104—the current pose of the robotic arm may be based on a pose of the second tracking device as indicated in the dataset received in the step 608. A known offset (e.g., a known spatial relationship) between the second tracking device and the robotic arm may be used to determine the current pose of the robotic arm from the pose of the second tracking device.

The method 600 also comprises comparing the expected pose and the current pose of the robotic arm (step 612). Comparing the expected pose and the current pose of the robotic arm yields a determination as to whether the robot has experienced undesired or unplanned movement. Comparing the current pose and the expected pose may include comparing one or more coordinates of the expected pose to one or more coordinates of the current pose using the processor.

In instances where the expected pose and the current pose match, then this may indicate that no undesired movement of the robotic arm (and therefore of the patient, given the connection between the robot and the patient) has occurred. In instances where the expected pose and the current pose do not match, then this may indicate that undesired movement of the robotic arm has occurred—whether due to unplanned or undesired movement of the robotic arm, miscalibration of the robot, movement of the patient, or otherwise. A determination that the expected pose of the robotic arm does not match the current pose of the robotic arm may mean, therefore, that the patient has moved and that a previously completed registration must be updated or replaced.

In some embodiments, the method 600 also comprises receiving a second dataset (step 616). The step 608 is the same as or similar to the step 408 described above.

Also in some embodiments, the method 600 comprises comparing the first dataset and the second dataset to determine if a relative pose of the robot has changed (step 620). The step 620 is the same as or similar to the step 416 described above, except that if the robotic arm has been intentionally moved in between the time that the first dataset was obtained and the time that the second dataset was obtained, then in making the comparison, the intended movement of the robotic arm must be taken into account. In other words, if the comparison demonstrates that the pose of the second tracking device affixed to the robotic arm is different in the second dataset than in the first dataset, then further processing is required to determine if the change in pose is attributable solely to intended movement of the robotic arm, or if some portion of the change in pose is attributable to unintended or undesired movement of the robot, and thus of the patient.

In some embodiments, the steps 616 and 620 may occur when the expected pose and the current pose of the robotic arm match as described in step 612. Also in some embodiments of the method 600, the steps 616 and 620 may be omitted, and the steps 608 and 612 may be relied upon to determine whether patient movement has possibly occurred.

The method 600 also comprises generating a notification when the relative pose has changed (or where the expected pose does not match the current pose) (step 624). The step 624 is the same as or similar to the step 420 described above. In some embodiments, the notification may also be generated by a processor, such as the processor 104, when the expected pose and the current pose of the robotic arm do not match as described in step 612. In at least some of the embodiments, the notification may include instructions for one or more of recalibrating the robot, repeating some or all of the registration process, or verifying a pose of one or more anatomical elements and/or any component on the robot using, for example, a probe such as a navigation probe.

The method 600 also comprises causing the notification to be displayed (step 628). The step 628 is the same as or similar to the step 424 described above.

It will be appreciated that one or more of the steps 604-620 may be repeated throughout a surgical procedure to verify that a previously completed registration remains accurate. In some embodiments one or more of the steps 604-620 may be repeated prior to a surgical step. In other embodiments one or more of the steps 604-620 may be continuously repeated throughout a duration of the surgical procedure to continuously monitor the patient and the table for relative movement.

The present disclosure encompasses embodiments of the method 600 that comprise more or fewer steps than those described above, and/or one or more steps that are different than the steps described above.

It will be appreciated that the methods 400 and/or 600 may include monitoring any number of tracking markers during a surgical procedure. For example, more than one tracking marker may be positioned on a patient. In another example, a tracking marker may be positioned on each of a table, a patient, and a robot. In embodiments where more than two tracking markers are monitored, one or more relative poses between different tracking markers may also be monitored.

As noted above, the present disclosure encompasses methods with fewer than all of the steps identified in FIGS. 4 and 6 (and the corresponding description of the methods 400, 600), as well as methods that include additional steps beyond those identified in FIGS. 4 and 6 (and the corresponding description of the methods 400 and 600). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for monitoring patient movement comprising:
a first tracking device affixed to a table;
a second tracking device configured to be affixed to an anatomical element, the anatomical element having a pose relative to the table;
a robotic arm positionable in any pose and configured to support an object;
at least one processor; and
at least one memory storing instructions for execution by the at least one processor that, when executed, cause the at least one processor to:
register a patient to a pre-operative image to yield a correlation between a coordinate system associated with the patient and a coordinate system associated with a navigation system, wherein the correlation is used to track the robotic arm relative to the anatomical element,
receive a first dataset, the first dataset containing a first image depicting the first tracking device and the second tracking device,
receive a second dataset, the second dataset containing a second image depicting the first tracking device and the second tracking device,
process each of the first image and the second image to identify the first tracking device and the second tracking device,
determine a first relative pose of the first tracking device relative to the second tracking device from the processed first image and a second relative pose of the first tracking device relative to the second tracking device from the processed second image,
compare the first relative pose and the second relative pose to determine if a relative pose of the first tracking device and the second tracking device has changed,
generate a notification when the relative pose of the first tracking device and the second tracking device has changed,
reregister the patient to the pre-operative image based on the notification indicating that the relative pose of the first tracking device and the second tracking device has changed, wherein reregistering the patient to the pre-operative image yields an updated correlation between the coordinate system associated with the patient and the coordinate system associated with the navigation system, and
use the updated correlation to automatically position the robotic arm relative to the anatomical element.

2. The system of claim 1, further comprising:
a user interface, and wherein the at least one memory stores additional instructions for execution by the at least one processor that, when executed, further cause the at least one processor to:
cause the notification to be displayed on the user interface.

3. The system of claim 1, wherein the notification includes instructions for performing one or more verification steps.

4. The system of claim 3, wherein the at least one memory stores additional instructions for execution by the at least one processor that, when executed, further cause the at least one processor to:
determine a spatial relationship between a patient and the second tracking device.

5. The system of claim 1, wherein the anatomical element is a vertebra.

6. The system of claim 1, wherein the navigation system comprises
an optical imaging device, the optical imaging device configured to obtain the first dataset and the second dataset.

7. The system of claim 1, wherein the second tracking device comprises a plurality of tracking devices.

8. A system for monitoring patient movement comprising:
a robotic arm positionable in any pose and configured to support an object;
a first tracking device affixed to a table;
a second tracking device affixed to the robotic arm, the robotic arm having a pose relative to the table;
at least one processor; and
at least one memory storing instructions for execution by the at least one processor that, when executed, cause the at least one processor to:
register a patient to a pre-operative image to yield a correlation between a coordinate system associated with the patient and a coordinate system associated with a navigation system, wherein the correlation is used to track the robotic arm,
receive a first dataset, the first dataset containing a first image depicting the first tracking device and the second tracking device,
receive a second dataset, the second dataset containing a second image depicting the first tracking device and the second tracking device,
process each of the first image and the second image to identify the first tracking device and the second tracking device,
determine a first relative pose of the first tracking device relative to the second tracking device from the processed first image and a second relative pose of the first tracking device relative to the second tracking device from the processed second image,
compare the first relative pose and the second relative pose to determine if a relative pose of the first tracking device and the second tracking device has changed,
generate a notification when the relative pose of the first tracking device and the second tracking device has changed,
reregister the patient to the pre-operative image based on the notification indicating that the relative pose of the first tracking device and the second tracking device has changed, wherein reregistering the patient to the pre-operative image yields an updated correlation between the coordinate system associated with the patient and the coordinate system associated with the navigation system, and
use the updated correlation to automatically position the robotic arm.

9. The system of claim 8, wherein the second tracking device is integrated with the robotic arm.

10. The system of claim 8, further comprising:
a user interface, and wherein the at least one memory stores additional instructions for execution by the at least one processor that, when executed, further cause the at least one processor to:
cause the notification to be displayed on the user interface.

11. The system of claim 8, wherein the notification includes instructions for performing one or more verification steps.

12. The system of claim 11, wherein the robotic arm is affixed to the table.

13. The system of claim 11, wherein the one or more verification steps includes verifying a pose of one or more anatomical elements using a navigation probe.

14. The system of claim 9, wherein the navigation system comprises
an optical imaging device, the optical imaging device configured to obtain the first dataset and the second dataset.

15. The system of claim 8, wherein the first dataset and the second dataset comprises image data.

16. The system of claim 8, wherein the first dataset and the second dataset comprises sensor data.

17. A system for monitoring patient movement comprising:
a first tracking device affixed to a table;
a second tracking device configured to be affixed to an anatomical element, the anatomical element having a pose relative to the table;
a robotic arm positionable in any pose and configured to support an object;
at least one processor; and
at least one memory storing instructions for execution by the at least one processor that, when executed, cause the at least one processor to:
register a patient to a pre-operative image to yield a correlation between a coordinate system associated with the patient and a coordinate system associated with a navigation system, wherein the correlation is used to track the robotic arm relative to the anatomical element,
receive a first dataset, the first dataset containing first sensor data corresponding to the first tracking device and the second tracking device,
receive a second dataset, the second dataset containing second sensor data corresponding to the first tracking device and the second tracking device,
process each of the first sensor data and the second sensor data to identify the first tracking device and the second tracking device,
determine a first relative pose of the first tracking device relative to the second tracking device from the processed first sensor data and a second relative pose of the first tracking device relative to the second tracking device from the processed second sensor data,
compare the first relative pose and the second relative pose to determine if a relative pose of the first tracking device and the second tracking device has changed,
generate a notification when the relative pose of the first tracking device and the second tracking device has changed,
reregister the patient to the pre-operative image based on the notification indicating that the relative pose of the first tracking device and the second tracking device has changed, wherein reregistering the patient to the pre-operative image yields an updated correlation between the coordinate system associated with the patient and the coordinate system associated with the navigation system, and
use the updated correlation to automatically position the robotic arm relative to the anatomical element.

18. The system of claim 17, further comprising at least one sensor that measures sensor data corresponding to the first tracking device and the second tracking device.

19. The system of claim 18, wherein the at least one sensor comprises at least one of an optical camera, an infrared camera, a 3D camera system, or a stereoscopic vision system.

* * * * *